United States Patent
Ren et al.

(10) Patent No.: US 11,201,935 B2
(45) Date of Patent: Dec. 14, 2021

(54) COOKING DEVICE-BASED RECIPE PUSHING METHOD AND APPARATUS

(71) Applicant: FOSHAN SHUNDE MIDEA ELECTRICAL HEATING APPLIANCES MANUFACTURING CO., LTD., Foshan (CN)

(72) Inventors: Pengbo Ren, Foshan (CN); Baizhong Ma, Foshan (CN); Qingsong Gu, Foshan (CN)

(73) Assignee: FOSHAN SHUNDE MIDEA ELECTRICAL HEATING APPLIANCES MANUFACTURING CO., LTD., Foshan (CN)

( * ) Notice: Subject to any disclaimer, the term of this patent is extended or adjusted under 35 U.S.C. 154(b) by 0 days.

(21) Appl. No.: 16/484,528

(22) PCT Filed: Nov. 21, 2017

(86) PCT No.: PCT/CN2017/112147
§ 371 (c)(1),
(2) Date: Aug. 8, 2019

(87) PCT Pub. No.: WO2018/149193
PCT Pub. Date: Aug. 23, 2018

(65) Prior Publication Data
US 2020/0036804 A1   Jan. 30, 2020

(30) Foreign Application Priority Data

Feb. 14, 2017   (CN) .................... 201710077668.X

(51) Int. Cl.
*H04L 29/08*   (2006.01)
*G16H 20/60*   (2018.01)
(Continued)

(52) U.S. Cl.
CPC ............ *H04L 67/26* (2013.01); *A47J 36/321* (2018.08); *G06F 16/90335* (2019.01);
(Continued)

(58) Field of Classification Search
CPC ....... H04L 67/12; H04L 67/10; H04L 67/306; H04L 67/22; H04L 67/26; H04L 67/24;
(Continued)

(56) References Cited

U.S. PATENT DOCUMENTS

2008/0082477 A1 * 4/2008 Dominowska ........ G06F 16/951
2008/0195607 A1 * 8/2008 Kutsumi ............ G06Q 30/0273
(Continued)

FOREIGN PATENT DOCUMENTS

| CN | 103637693 A | 3/2014 |
|---|---|---|
| CN | 104957965 A | 10/2015 |

(Continued)

OTHER PUBLICATIONS

World Intellectual Property Organization (WIPO) International Search Report for PCT/CN2017/112147 dated Feb. 26, 2018 6 Pages.
(Continued)

*Primary Examiner* — Djenane M Bayard
(74) *Attorney, Agent, or Firm* — Anova Law Group, PLLC

(57) ABSTRACT

A recipe pushing method includes receiving cooking device product information of a cooking device transmitted by a terminal device via a cooking service application, extracting a recipe preference characteristic of a user according to a history of the user browsing recipes in the cooking service application and a preset filtering condition, generating a recommended recipe matching the cooking device product information according to the recipe preference characteristic, and transmitting the recommended recipe to the cooking service application.

17 Claims, 4 Drawing Sheets

(51) Int. Cl.
*A47J 36/32* (2006.01)
*G06F 16/903* (2019.01)

(52) U.S. Cl.
CPC .............. G16H 20/60 (2018.01); H04L 67/22 (2013.01); H04L 67/24 (2013.01); H04L 67/306 (2013.01)

(58) Field of Classification Search
CPC ............. H04L 67/125; H04L 2463/101; H04L 63/0853; H04L 63/101; H04L 67/02; H04L 67/325; H04L 67/34; H04L 69/08
See application file for complete search history.

(56) References Cited

U.S. PATENT DOCUMENTS

| | | | | |
|---|---|---|---|---|
| 2014/0089321 A1* | 3/2014 | Engel | .................. | G06F 16/9535 707/748 |
| 2014/0144977 A1* | 5/2014 | Argue | ................ | G06Q 30/0633 235/375 |
| 2014/0158753 A1* | 6/2014 | Sisselman | ........... | G06F 16/9554 235/375 |
| 2018/0167467 A1* | 6/2018 | Chen | ........................ | H04L 67/36 |
| 2018/0253459 A1* | 9/2018 | Srinivasan Natesan et al. | ........... | G06Q 10/00 |

FOREIGN PATENT DOCUMENTS

| CN | 105030040 A | 11/2015 |
|---|---|---|
| CN | 105030041 A | 11/2015 |
| CN | 105607508 A | 5/2016 |
| CN | 105701092 A | 6/2016 |
| CN | 105930659 A | 9/2016 |
| CN | 106202565 A | 12/2016 |
| CN | 106372258 A | 2/2017 |

OTHER PUBLICATIONS

World Intellectual Property Organization (WIPO) Written Opinion for PCT/CN2017/112147 dated Feb. 26, 2018 7 Pages.
The China National Intellectual Property Administration (CNIPA) The First Office Action for 201710077668.X dated Feb. 25, 2020 16 Pages (With translation).
The China National Intellectual Property Administration (CNIPA) The Second Office Action for 201710077668.X dated Sep. 21, 2020 15 Pages (With translation).

* cited by examiner

COOKING DEVICE-BASED RECIPE PUSHING METHOD AND APPARATUS

TECHNICAL FIELD

The present disclosure relates to the technical field of household appliances, and more particularly relates to a cooking device-based recipe pushing method and apparatus.

BACKGROUND

In order to facilitate the lives of users, cooking devices are becoming more and more diverse. However, the lack of in-depth knowledge of the cooking devices by most users causes good cooking devices to fail in achieving their best effects.

In addition, with the development of information diversification, a variety of cooking methods are shown to the users. As a result, the users select recipes that do not match the cooking devices for cooking, or the recommended cooking methods may not meet the individual needs of the users, resulting in inconvenience in use for the users.

SUMMARY OF THE DISCLOSURE

The present disclosure is directed to at least solving one of the technical problems in the relevant art to a certain extent.

Thus, the first objective of the present disclosure is to provide a cooking device-based recipe pushing method. The method can recommend a suitable recipe that matches cooking device product information and meets personal preference, which allows the cooking device to perform the maximum function and bring convenience to a user for use, thereby meeting an individual need of the user to the maximum extent and enhance the user life experience.

The second objective of the present disclosure is to provide a cooking device-based recipe pushing apparatus.

In order to achieve the foregoing objectives, the embodiment in the first aspect of the present disclosure provides a cooking device-based recipe pushing method, including: receiving cooking device product information transmitted by a terminal device by means of a cooking service application; extracting a recipe preference characteristic of a user according to recipes in the cooking service application browsed by the user and a preset filtering condition; generating, according to the recipe preference characteristic, a recommended recipe matching the cooking device product information; and transmitting the recommended recipe to the cooking service application so as to provide the user with the same.

The cooking device-based recipe pushing method according to the embodiment of the present disclosure receives the cooking device product information transmitted by the terminal device by means of the cooking service application, extracts the recipe preference characteristic of the user according to recipes in the cooking service application browsed by the user and the preset filtering condition, then generates, according to the recipe preference characteristic, the recommended recipe matching the cooking device product information, and finally, transmits the recommended recipe to the cooking service application so as to provide the user with the same. Therefore, the suitable recipe that matches the cooking device product information and conforms to the personal preference may be recommended to the user, which allows the cooking device to perform the maximum function and bring convenience to the user for use, thereby meeting an individual need of the user to the maximum extent and enhance the user life experience.

In addition, the cooking device-based recipe pushing method according to the foregoing embodiment of the present disclosure also has the following additional technical features.

Optionally, receiving the cooking device product information transmitted by the terminal device by means of the cooking service application includes: receiving the cooking device product information transmitted by means of the cooking service application after the terminal device scans a two-dimensional code of the cooking device.

Optionally, extracting the recipe preference characteristic of the user according to the recipes in the cooking service application browsed by the user and the preset filtering condition includes: detecting whether a browsing duration of the user for a target recipe in the cooking service application is greater than or equal to a preset first threshold value, and extracting the recipe preference characteristic of the user according to information of the target recipe if YES; and/or, detecting whether a browsing frequency of the user for the target recipe in the cooking service application is greater than or equal to a preset second threshold value, and extracting the recipe preference characteristic of the user according to the information of the target recipe if YES.

Optionally, before transmitting the recommended recipe to the cooking service application so as to provide the user with the same, the method also includes: acquiring auxiliary preference information of the user; and generating, according to the recipe preference characteristic and the auxiliary preference information, the recommended recipe matching the cooking device product information.

Optionally, acquiring the auxiliary preference information of the user includes: receiving an application login request including user information transmitted by the user by means of the terminal device; permitting a user account corresponding to the user information to log in the cooking service application if the user information is verified, according to pre-stored registration information, to be legal; and acquiring user attribute information according to the registration information of the user account.

Optionally, acquiring the auxiliary preference information of the user includes: acquiring interactive information between the user and other applications by means of the cooking service application; and acquiring user associated information according to the interactive information.

Optionally, acquiring the auxiliary preference information of the user includes: acquiring location information of the user.

Optionally, after transmitting the recommended recipe to the cooking service application so as to provide the user with the same, the method also includes: receiving evaluation information, transmitted by the terminal device by means of the cooking service application, of the user for the recommended recipe; and optimizing the generated recommended recipe corresponding to the user according to the evaluation information.

In addition, the embodiment of the present disclosure further provides a machine readable storage medium. The machine readable storage medium stores instructions used to cause the cooking device to implement the foregoing recipe pushing method.

In order to achieve the foregoing objective, the embodiment in the second aspect of the present disclosure provides a cooking device-based recipe pushing apparatus, including: a first receiving module, used for receiving cooking device product information transmitted by a terminal device by means of a cooking service application; an extracting module, used for extracting a recipe preference characteristic of a user according to recipes in the cooking service application browsed by the user and a preset filtering condition; a first generating module, used for generating, according to the recipe preference characteristic, a recommended recipe matching the cooking device product information; and a providing module, used for transmitting the recommended recipe to the cooking service application so as to provide the user with the same.

The cooking device-based recipe pushing apparatus according to the embodiment of the present disclosure receives the cooking device product information transmitted by the terminal device by means of the cooking service application, extracts the recipe preference characteristic of the user according to recipes in the cooking service application browsed by the user and the preset filtering condition, then generates, according to the recipe preference characteristic, the recommended recipe matching the cooking device product information, and finally, transmits the recommended recipe to the cooking service application so as to provide the user with the same. Therefore, the suitable recipe that matches the cooking device product information and conforms to the personal preference may be recommended to the user, which allows the cooking device to perform the maximum function and bring convenience to the user for use, thereby meeting an individual need of the user to the maximum extent and enhance the user life experience.

In addition, the cooking device-based recipe pushing apparatus according to the foregoing embodiment of the present disclosure also has the following additional technical features.

Optionally, the first receiving module is used for receiving the cooking device product information transmitted by means of the cooking service application after the terminal device scans a two-dimensional code of the cooking device.

Optionally, the extracting module is used for: detecting whether a browsing duration of the user for a target recipe in the cooking service application is greater than or equal to a preset first threshold value, and extracting the recipe preference characteristic of the user according to information of the target recipe if YES; and/or, detecting whether a browsing frequency of the user for the target recipe in the cooking service application is greater than or equal to a preset second threshold value, and extracting the recipe preference characteristic of the user according to the information of the target recipe if YES.

Optionally, the device also includes: an acquiring module, used for acquiring auxiliary preference information of the user; and a second generating module, used for generating, according to the recipe preference characteristic and the auxiliary preference information, the recommended recipe matching the cooking device product information.

Optionally, the acquiring module is used for: receiving an application login request including user information transmitted by the user by means of the terminal device; permitting a user account corresponding to the user information to log in the cooking service application if the user information is verified, according to pre-stored registration information, to be legal; and acquiring user attribute information according to the registration information of the user account.

Optionally, the acquiring module is also used for: acquiring interactive information between the user and other applications by means of the cooking service application; and acquiring user associated information according to the interactive information.

Optionally, the acquiring module is also used for: acquiring location information of the user.

Optionally, the device also includes: a second receiving module, used for receiving evaluation information, transmitted by the terminal device by means of the cooking service application, of the user for the recommended recipe; and an optimizing module, used for optimizing the generated recommended recipe corresponding to the user according to the evaluation information.

Additional aspects and advantages of the present disclosure will be described in the descriptions below, part of which will be readily apparent from the following descriptions or learnt via practice of the present disclosure.

DESCRIPTION OF THE DRAWINGS

The foregoing and/or additional aspects and advantages of the present disclosure will become apparent and easily understandable from the descriptions of embodiments with reference to accompanying drawings. In the drawings.

DETAILED DESCRIPTION OF THE EMBODIMENTS

Figure 1:
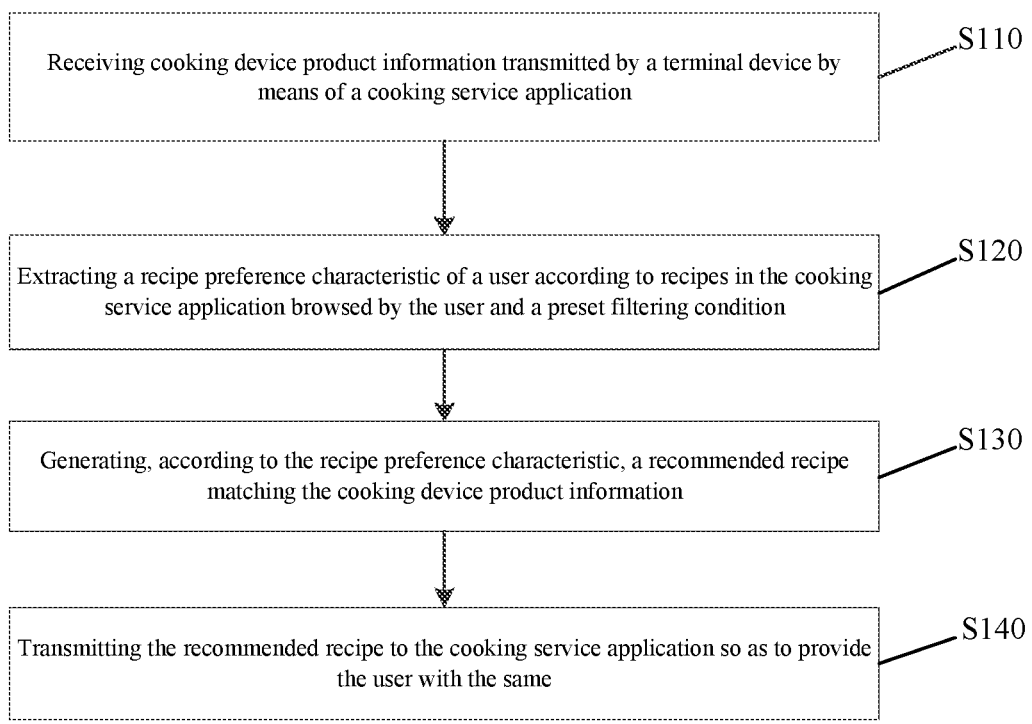
FIG. 1 is a process diagram of a cooking device-based recipe pushing method according to an embodiment of the present disclosure.

Embodiments of the present disclosure are described below in detail. Examples of the embodiments are illustrated in the drawings. Same or similar reference numbers always represent like or similar elements or elements having like or similar functions. The embodiments described below with reference to the drawings are exemplary, and are intended to interpret the present disclosure, but not understood as limiting the present disclosure.

A cooking device-based recipe pushing method and apparatus of the embodiments of the present disclosure are described below with reference to the drawings.

At present, cooking devices in the life are becoming more and more diverse, and in order to achieve balanced nutrition in a diet, a user usually subscribes to some recipes through a terminal device, so that the user can cook according to recommended recipes.

However, in the above process, the recommended recipes neither understand cooking device product information nor understand the personal preference of the user, so that the recommended recipes may not be suitable for the cooking device to perform its maximum function and meet the user's need.

In order to avoid the above problems, the embodiment of the present disclosure provides a cooking device-based recipe pushing method to determine which recipes the user prefers by the recipes browsed by the user and recommend a recipe conforming to a personal preference to the user in combination with the cooking device product information, so that the cooking device may perform the maximum function and facilitate use by the user, thereby meeting the individual need of the user to the maximum extent and enhancing the life experience of the user. Details are as follows.

FIG. 1 is a process diagram of a cooking device-based recipe pushing method according to an embodiment of the present disclosure.

As shown in FIG. 1, the cooking device-based recipe pushing method includes the following steps.

Step 110, cooking device product information transmitted by a terminal device by means of a cooking service application is received.

Specifically, the cooking device is not limited to one or more of household appliances such as an electric cooker, an electric pressure cooker and an induction cooker.

It can be understood that different cooking devices are different in their cooking processes and main functions and also have different effects with same recipes. In the embodiment of the present disclosure, in order to recommend a recipe matching the cooking device to the user, that is, in order to enable the cooking device to achieve a good cooking effect with the recommended recipe, the cooking device product information needs to be considered in the process of generating the recommended recipe.

The cooking device product information may include the type of the cooking device, main functions and the like. For example, if the cooking device is the electric cooker, the cooking device product information may include electric cooker, rice cooking, congee cooking, soup cooking and the like. Therefore, a poor user life experience, caused by the electric cooker not performing its maximum function if the recipe recommended for the electric cooker is a fried dish-series recipe such as "Fish Flavored Pork Slice," is avoided.

Specifically, the cooking device product information may be transmitted by means of the cooking service application in the terminal device to a server (which may be a local server or a cloud server or the like). There are a variety of methods for acquiring the cooking device product information by the terminal device, and the methods may be selectively set according to an actual application requirement. Examples are as follows.

In the first example, the cooking device product information transmitted by means of the cooking service application after the terminal device scans a two-dimensional code of the cooking device is received.

The cooking device product information is pre-stored in a two-dimensional code form on the cooking device such that the cooking device product information may be acquired by means of scanning the two-dimensional code when needed, and the operation is simple and convenient and facilitates the use by the user.

In the second example, the corresponding cooking device product information manually input by the user in the cooking service application in the terminal device is received.

Step 120, a recipe preference characteristic of the user is extracted according to recipes in the cooking service application browsed by the user and a preset filtering condition.

Specifically, the personal preference of the user needs to be considered after the cooking device product information is acquired. For example, for such a situation that the cooking device is the electric cooker and the recommended recipe is corn and sparerib soup, and the user does not like to eat pork, the need of the user may not be met.

Further, the recipe preference characteristic, i.e. a preferred recipe characteristic of the user, is acquired. There are a variety of methods for extracting the recipe preference characteristic of the user according to the recipes in the cooking service application browsed by the user and the preset filtering condition, and the methods may be set according to an actual application requirement. Examples are as follows.

In the first example, whether a browsing duration of the user on a target recipe in the cooking service application is greater than or equal to a preset first threshold value is detected, and if yes, the recipe preference characteristic of the user is extracted according to information of the target recipe.

In the second example, whether a browsing frequency of the user on the target recipe in the cooking service application is greater than or equal to a preset second threshold value is detected, and if yes, the recipe preference characteristic of the user is extracted according to information of the target recipe.

The filtering condition is selectively set according to an actual application requirement, such as whether browsing duration of the user for the target recipe in the cooking service application is greater than or equal to the preset first threshold value, whether the browsing frequency of the user for the target recipe in the cooking service application is greater than or equal to the preset second threshold value or the like.

It should be noted that the recipe preference characteristic of the user may be acquired by one, two or more of the above methods (the final recipe characteristic of the user may be acquired by calculation with different weights assigned thereto, or the like). Therefore, the requirement of the user may be met to the maximum extent.

Step 130, a recommended recipe matching the cooking device product information is generated according to the recipe preference characteristic.

Step 140, the recommended recipe is transmitted to the cooking service application so as to be provided to the user.

Specifically, after the recipe preference characteristic is acquired, the recommended recipe matching the cooking device product information is acquired according to the recipe preference characteristic from a database pre-stored in a local server or in a way of networking a cloud server or the like.

Further, there are a variety of methods for transmitting the recommended recipe to the cooking service application so as to provide the user with the same. Examples are as follows.

In the first example, the recommended recipe is displayed on the terminal device by means of the cooking service application.

The method for recommending the recipe is not limited to displaying, and also may be voice broadcasting or the like so as to further enhance the user life experience.

In the second example, the recommended recipe is displayed on the cooking device by means of the cooking service application, or the recommended recipe is broadcast in voice by the cooking device.

It should be noted that relevant cooking service applications also may be installed on the cooking device.

It can be understood that the recommended recipe may be subsequently regularly pushed to the user after being determined, so as to facilitate the use by the user.

According to the above, the cooking device-based recipe pushing method according to the embodiment of the present disclosure receives the cooking device product information transmitted by the terminal device by means of the cooking service application, extracts the recipe preference characteristic of the user according to the recipes in the cooking service application browsed by the user and the preset filtering condition, then generates, according to the recipe preference characteristic, the recommended recipe matching the cooking device product information, and finally, transmits the recommended recipe to the cooking service application so as to provide the user with the same. Therefore, the suitable recipe that matches the cooking device product information and conforms to the personal preference may be recommended to the user, which allows the cooking device to perform the maximum function and bring convenience to the user for use, thereby meeting an individual need of the user to the maximum extent and enhance the user life experience.

Figure 2:
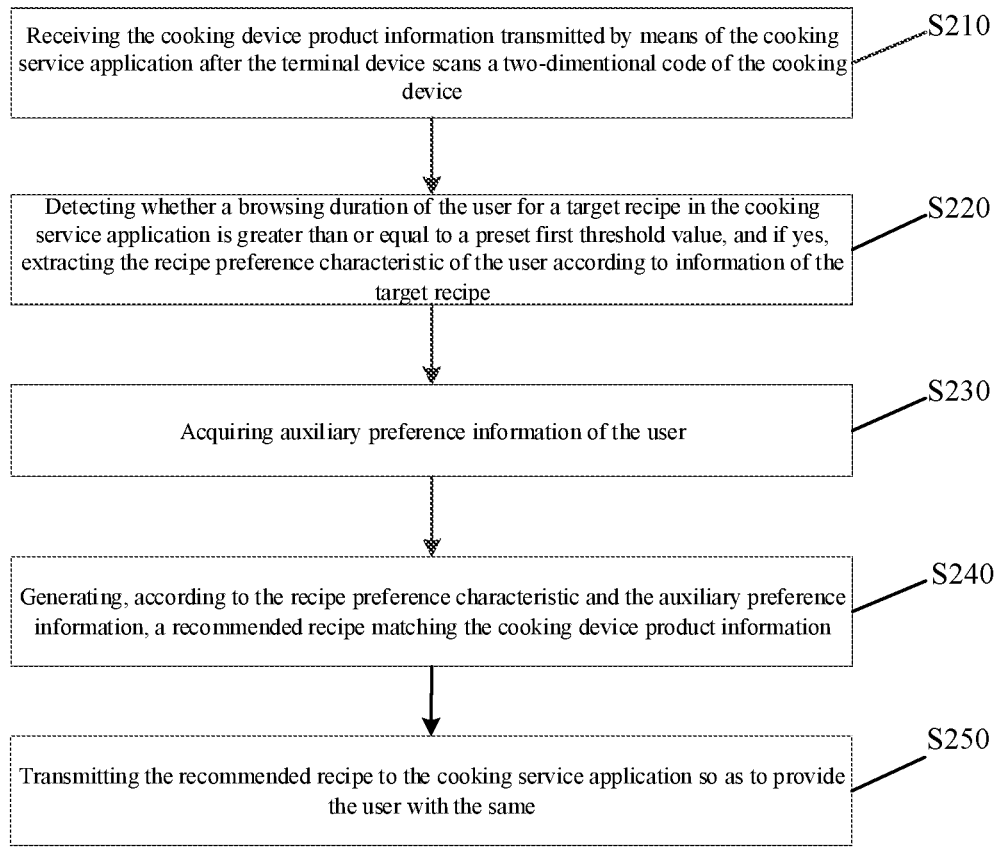
FIG. 2 is a process diagram of a cooking device-based recipe pushing method according to another embodiment of the present disclosure.

FIG. 2 is a process diagram of a cooking device-based recipe pushing method according to another embodiment of the present disclosure.

As shown in FIG. 2, the cooking device-based recipe pushing method includes the following steps.

Step 210, cooking device product information transmitted by means of a cooking service application after a terminal device scans a two-dimensional code of a cooking device is received.

Specifically, for example, the cooking device product information is acquired in advance and converted into a two-dimensional code, which is stuck on the cooking device. When the cooking device product information is needed, the cooking device product information transmitted by means of the cooking service application may be received after the terminal device scans the two-dimensional code of the cooking device.

For specific descriptions of the cooking device product information, reference can be made to Step 110, and no more details will be described here.

Step 220, whether a browsing duration of the user for a target recipe in the cooking service application is greater than or equal to a preset first threshold value is detected, and if yes, the recipe preference characteristic of the user is extracted according to information of the target recipe.

Specifically, there are many recipes in the cooking device application, and the user can browse and choose the recipes he or she likes. It can be understood that the user may stay for a while to acquire more recipe information when interested in a certain recipe. Therefore, the general browsing duration may be set as the first threshold value according to an actual application requirement. The browsing duration of the user for the target recipe in the cooking service application being greater than or equal to the preset first threshold value indicates that the user is interested in the target recipe.

Specifically, when the user browses the recipes, there are a plurality of target recipes having the browsing durations greater than or equal to the preset first threshold value, so the plurality of target recipes may be processed to extract the recipe preference characteristic of the user. For example, the browsing durations of the user for three target recipes: "Fish Flavored Pork Slice," "Kung Pao Chicken" and "Fish Filets in Hot Chili Oil" are greater than or equal to the preset first threshold value, and this means that the user is interested in Sichuan cuisine. Therefore, the recipe preference characteristic of the user may be extracted as Sichuan cuisine or fondness for spicy food or the like.

Step 230, auxiliary preference information of the user is acquired.

Step 240, a recommended recipe matching the cooking equipment product information is generated according to the recipe preference characteristic and the auxiliary preference information.

Step 250, the recommended recipe is transmitted to the cooking service application so as to be provided to the user.

Specifically, in order to further meet the user need, i.e., to meet the user need to the maximum extent, the auxiliary preference information of the user may be acquired. There are various types of auxiliary preference information of the user, and different methods are used for acquiring different types of auxiliary preference information of the user. The methods may be selectively set according to an actual application requirement. Examples are as follows.

In the first example, an application login request including user information transmitted by the user by means of the terminal device is received, and a user account corresponding to the user information is permitted to log in the cooking service application if the user information is verified to be legal according to pre-stored registration information, and user attribute information is acquired according to the registration information of the user account.

Specifically, for the security of information, general cooking service applications all require corresponding account registration and login for corresponding control and management. Usually, the user may store the user attribute information (such as gender, age, hobbies, etc.) in advance when registering an account.

Therefore, the user account corresponding to the user information is permitted to log in the cooking service application when the application login request including the user information transmitted by the user by means of the terminal device is received and the user information is verified to be legal according to the pre-stored registration information, so that the corresponding user attribute information may be acquired. The personal preference, healthy life and the like of the user can be analyzed to further enhance the user life experience.

In the second example, interactive information between the user and other applications by means of the cooking service application is acquired, and user associated information is acquired according to the interactive information.

Specifically, the interactive information between the cooking service application and other applications may be understood to be that when the user browsing the recipes in the cooking service application wishes to share the recipes with friends in the WeChat application, the user directly transmits the recipes to the relevant friends through corresponding operations, or the user transmits the recipes to the Weibo application for sharing, etc. Therefore, according to the above interactive information, the user associated information, such as recipes the user prefers, recipes that family members of the user prefer, and a healthy lifestyle of the user, may be acquired. In the third example, location information of the user is acquired.

Specifically, the location information of the user may be acquired by using a positioning system of the terminal device or in a way of manually inputting the location information by the user. For example, if the location information of the user is Guangzhou, the user need may be further met according to local diet habits and the like.

Further, the recommended recipe matching the cooking device product information is acquired according to the extracted recipe preference characteristic and the auxiliary preference information from the database pre-stored in the local server or by searching in a search engine such as Baidu or Google via cloud server networking.

Further, the recommended recipe is displayed on the terminal device by means of the cooking service application. The method for recommending the recipe is not limited to displaying, and may also be voice broadcasting or the like so as to further enhance the user life experience.

According to the above, the cooking device-based recipe pushing method according to the embodiment of the present disclosure receives the cooking device product information transmitted by the terminal device by means of the cooking service application, extracts the recipe preference characteristic of the user according to the recipes in the cooking service application browsed by the user and the preset filtering condition, then acquires the auxiliary preference information of the user and generates, according to the recipe preference characteristic and the auxiliary preference information, the recommended recipe matching the cooking device product information, and finally, transmits the recommended recipe to the cooking service application so as to provide the user with the same. Therefore, the suitable recipe that matches the cooking device product information and conforms to the personal preference may be recommended to the user, which allows the cooking device to perform the maximum function and bring convenience to the user for use, thereby meeting an individual need of the user to the maximum extent and enhance the user life experience.

Based on the foregoing embodiments, after the recommended recipe is transmitted to the cooking service application so as to be provided to the user, whether the recommended recipe meets the need of the user to the maximum extent is also further determined according to a feedback result of the user on the recommended recipe, which is described in detail below in connection with FIG. 3.

Figure 3:
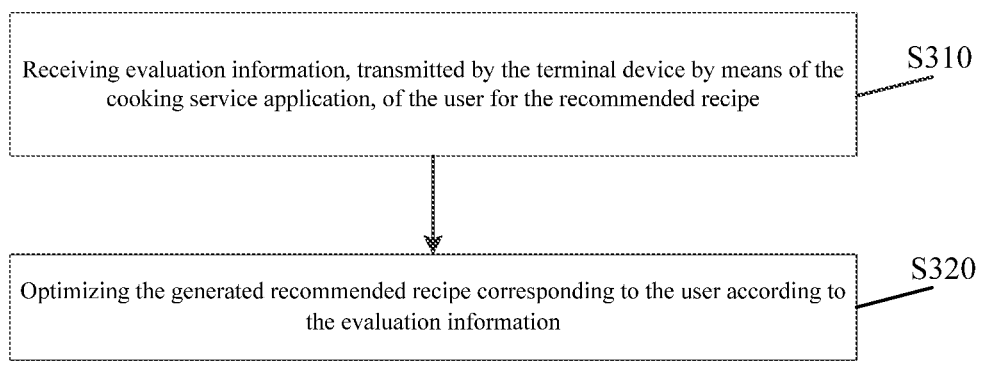
FIG. 3 is a process diagram of a cooking device-based recipe pushing method according to yet another embodiment of the present disclosure.

FIG. 3 is a process diagram of a cooking device-based recipe pushing method according to yet another embodiment of the present disclosure.

As shown in FIG. 3, after Step 140 or Step 250, the method also includes the following steps.

Step 310, evaluation information, transmitted by the terminal device by means of the cooking service application, of the user for the recommended recipe is received.

Step 320, the generated recommended recipe corresponding to the user is optimized according to the evaluation information.

Specifically, the user may love, like or dislike the recommended recipe, and may evaluate the recommended recipe by means of digital rating, star rating, inputting of comment information and/or the like, which can be transmitted as the evaluation information to a server through the cooking service application in the terminal device, so that the server may further optimize the recommended recipe according to the evaluation information.

Specifically, if the user likes the recommended recipe, suitable related recommended recipes are continuously pushed to the user in an optimized manner; and if the user dislikes the recommended recipe, matching is recalculated, and new recommended recipes are pushed to the user till the user is satisfied with a certain recipe.

It can be understood that the above process is a process of continuous optimization based on the health, the preference and/or the like of the user, so that the health of and nutrition for the user may be determined while the tasting effect is met, so as to realize a diet therapy function.

Thus, through the above-mentioned continuous optimization method, the recommended recipe that meets the user need to the maximum extent may be provided, and the healthy life of the user may be continuously managed to improve the quality of life of the user.

In order to achieve the foregoing embodiments, the present disclosure further provides a cooking device-based recipe pushing apparatus.

Figure 4:
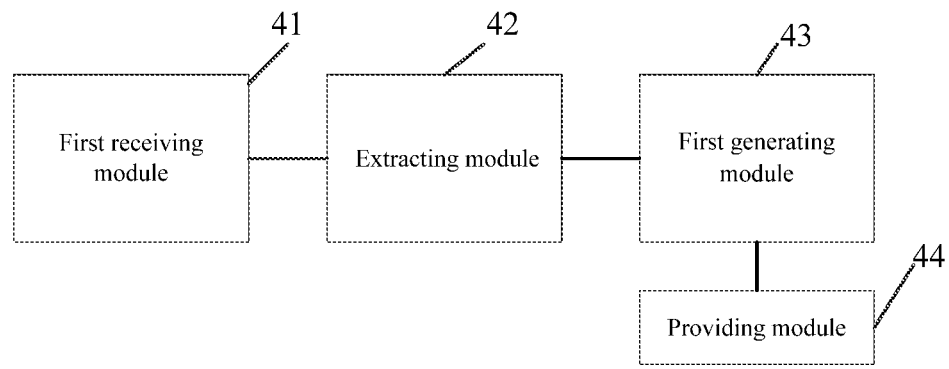
FIG. 4 is a structural schematic diagram of a cooking device-based recipe pushing apparatus according to an embodiment of the present disclosure.

FIG. 4 is a structural schematic diagram of a cooking device-based recipe pushing apparatus according to an embodiment of the present disclosure.

As shown in FIG. 4, the cooking device-based recipe pushing apparatus includes: a first receiving module 41, an extracting module 42, a first generating module 43 and a providing module 44.

The first receiving module 41 is used for receiving cooking device product information transmitted by a terminal device by means of a cooking service application.

The extracting module 42 is used for extracting a recipe preference characteristic of a user according to recipes in the cooking service application browsed by the user and a preset filtering condition.

The first generating module 43 is used for generating, according to the recipe preference characteristic, a recommended recipe matching the cooking device product information.

The providing module 44 is used for transmitting the recommended recipe to the cooking service application so as to provide the user with the same.

Specifically, in an embodiment of the present disclosure, the first receiving module 41 is used for receiving the cooking device product information transmitted by means of the cooking service application after the terminal device scans a two-dimensional code of the cooking device.

Specifically, in one embodiment of the present disclosure, the extracting module is used for: detecting whether a browsing duration of the user for a target recipe in the cooking service application is greater than or equal to a preset first threshold value, and if ye, extracting the recipe preference characteristic of the user according to information of the target recipe; and/or, detecting whether a browsing frequency of the user for the target recipe in the cooking service application is greater than or equal to a preset second threshold value, and if yes, extracting the recipe preference characteristic of the user according to the information of the target recipe.

It should be noted that the foregoing explanation of the embodiment of the cooking device-based recipe pushing method is also applicable to the cooking device-based recipe pushing apparatus in the present embodiment, and no more details will be described here.

According to the above, the cooking device-based recipe pushing apparatus according to the embodiment of the present disclosure receives the cooking device product information transmitted by the terminal device by means of the cooking service application, extracts the recipe preference characteristic of the user according to the recipes in the cooking service application browsed by the user and the preset filtering condition, then generates, according to the recipe preference characteristic, the recommended recipe matching the cooking device product information, and finally, transmits the recommended recipe to the cooking service application so as to provide the user with the same. Therefore, the suitable recipe that matches the cooking device product information and conforms to the personal preference may be recommended to the user, which allows the cooking device to perform the maximum function and bring convenience to the user for use, thereby meeting an individual need of the user to the maximum extent and enhance the user life experience.

In order to clearly describe the above embodiment, the present embodiment provides another cooking device-based recipe pushing apparatus.

Figure 5:
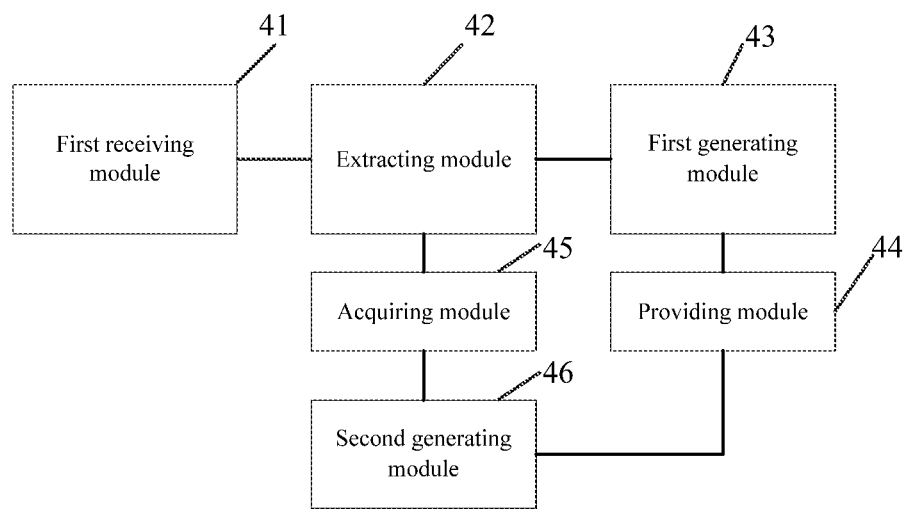
FIG. 5 is a structural schematic diagram of a cooking device-based recipe pushing apparatus according to another embodiment of the present disclosure.

FIG. 5 is a structural schematic diagram of a cooking device-based recipe pushing apparatus according to another embodiment of the present disclosure. As shown in FIG. 5, on the basis of the above embodiment, the device also includes: an acquiring module 45 and a second generating module 46.

The acquiring module 45 is used for acquiring auxiliary preference information of the user.

The second generating module 46 is used for generating, according to the recipe preference characteristic and the auxiliary preference information, the recommended recipe matching the cooking device product information.

Further, in one possible implementation mode of the embodiment of the present disclosure, the acquiring module 45 is used for: receiving an application login request including user information transmitted by the user by means of the terminal device; permitting a user account corresponding to the user information to log in the cooking service application if the user information is verified to be legal according to pre-stored registration information; and acquiring user attribute information according to the registration information of the user account.

Further, in one possible implementation mode of the embodiment of the present disclosure, the acquiring module 45 is also used for: acquiring interactive information between the user and other applications by means of the cooking service application; and acquiring user associated information according to the interactive information.

Further, in one possible implementation mode of the embodiment of the present disclosure, the acquiring module 45 is also used for: acquiring location information of the user.

It should be noted that the foregoing explanation of the embodiment of the cooking device-based recipe pushing method is also applicable to the cooking device-based recipe pushing apparatus in the present embodiment, and no more details will be described here.

According to the above, the cooking device-based recipe pushing apparatus according to the embodiment of the present disclosure receives the cooking device product information transmitted by the terminal device by means of the cooking service application, extracts the recipe preference characteristic of the user according to the recipes in the cooking service application browsed by the user and the preset filtering condition, then acquires the auxiliary preference information of the user and generates, according to the recipe preference characteristic and the auxiliary preference information, the recommended recipe matching the cooking device product information, and finally, transmits the recommended recipe to the cooking service application so as to provide the user with the same. Therefore, the suitable recipe that matches the cooking device product information and conforms to the personal preference may be recommended to the user, which allows the cooking device to perform the maximum function and bring convenience to the user for use, thereby meeting an individual need of the user to the maximum extent and enhance the user life experience.

Based on the foregoing embodiments, after the recommended recipe is transmitted to the cooking service application so as to be provided to the user, whether the recommended recipe meets the need of the user to the maximum extent is also further determined according to a feedback result of the user on the recommended recipe, which is described in more detail below in connection with FIG. 6.

Figure 6:
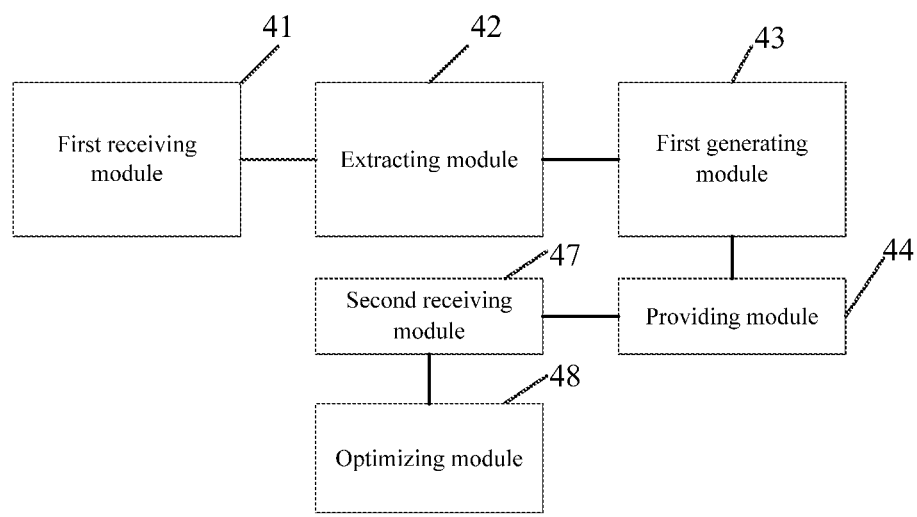
FIG. 6 is a structural schematic diagram of a cooking device-based recipe pushing apparatus according to yet another embodiment of the present disclosure.

FIG. 6 is a structural schematic diagram of a cooking device-based recipe pushing apparatus according to yet another embodiment of the present disclosure. As shown in FIG. 6, on the basis of FIG. 4, the device also includes: a second receiving module 47 and an optimizing module 48.

The second receiving module 47 is used for receiving evaluation information, transmitted by the terminal device by means of the cooking service application, of the user for the recommended recipe.

The optimizing module 48 is used for optimizing the generated recommended recipe corresponding to the user according to the evaluation information.

Specifically, the user may love, like or dislike the recommended recipe, and may evaluate the recommended recipe by means of digital rating, star rating, inputting of comment information and/or the like, which can be transmitted as the evaluation information to a server through the cooking service application in the terminal device, so that the server may further optimize the recommended recipe according to the evaluation information.

Specifically, if the user likes the recommended recipe, suitable related recommended recipes are continuously pushed to the user in an optimized manner; and if the user dislikes the recommended recipe, matching is recalculated, and new recommended recipes are pushed to the user till the user is satisfied with a certain recipe.

It can be understood that the above process is a process of continuous optimization based on the health, the preference and/or the like of the user, so that the health of and nutrition for the user may be determined while the tasting effect is met, so as to realize a diet therapy function.

Thus, through the above-mentioned continuous optimization method, the recommended recipe that meets the user need to the maximum extent may be provided, and the healthy life of the user may be continuously managed to improve the quality of life of the user.

In the descriptions of the present description, descriptions with reference to terms "an embodiment," "some embodiments," "example," "specific example" or "some examples" and the like means that specific features, structures, materials or characteristics described in the embodiments or examples are included in at least one embodiment or example of the present disclosure. In the present description, the schematic representations of the above terms are not necessarily directed to the same embodiments or examples. Furthermore, the particular features, structures, materials or characteristics described herein may be combined in a suitable manner in any one or more embodiments or examples. In addition, those skilled in the art can make connections and combinations to different embodiments or examples described in the preset description and features of different embodiments or examples without conflict.

Moreover, terms "first" and "second" are used for descriptive purposes only and are not to be construed as indicating or implying a relative importance or implicitly indicating the number of technical features indicated. Thus, features defining "first" or "second" may include at least one of the features, either explicitly or implicitly. In the description of the present disclosure, the meaning of "a plurality of" is at least two, such as two, three, etc., unless specifically defined otherwise.

Any process or method descriptions in the flowcharts or otherwise described herein may be understood as representing modules, segments or portions of codes comprising one or more executable instructions for implementing steps of a customized logic function or process, and the scope of the preferred implementation modes of the present disclosure includes additional implementations, in which the functions may be performed in a substantially simultaneous manner or in an opposite order depending on the functions involved, not in the order shown or discussed. It will be understood by those skilled in the art to which the embodiments of the present disclosure pertain.

It should be understood that respective portions of the present disclosure may be implemented via hardware, software, firmware or a combination thereof. In the foregoing implementation modes, multiple steps or methods may be implemented via software or firmware stored in a memory and executed by a suitable instruction execution system. For example, if the steps or methods are implemented via hardware, as in another implementation mode, they may be implemented by any one or a combination of the following techniques well known in the art: a discrete logic circuit having a logic gate circuit for implementing logic functions on data signals, a specific integrated circuit having an appropriate combinational logic gate circuit, a programmable gate array (PGA), a field programmable gate array (FPGA), etc.

Those of ordinary skill in the art can understand that all or part of the steps for implementing the methods of the above embodiments may be completed by instructing related hardware by a program, and the program may be stored in a machine readable storage medium. When executed, the program includes one or a combination of the steps of the method embodiments.

In addition, functional units in each embodiment of the present disclosure may be integrated into one processing module, or the units may exist physically independently, or two or more units may be integrated into one module. The above integrated modules may be implemented in the form of hardware or in the form of software functional modules. The integrated modules may also be stored in a computer readable storage medium if implemented in the form of software functional modules and sold or used as stand-alone products.

The above-mentioned storage medium may be a read only memory, a magnetic disk or an optical disk or the like. Although the embodiments of the present disclosure have been shown and described above, it can be understood that the foregoing embodiments are illustrative and are not to be construed as limiting the scope of the present disclosure. Those of ordinary skill in the art can make changes, modifications, replacements and variations to the foregoing embodiments within the scope of the present disclosure.

The invention claimed is:

1. A recipe pushing method comprising:
receiving cooking device product information of a cooking device transmitted by a terminal device via a cooking service application;
extracting a recipe preference characteristic of a user according to a history of the user browsing recipes in the cooking service application and a preset filtering condition;
acquiring auxiliary preference information of the user, including:
acquiring interactive information related to an interaction between the user and another application via the cooking service application; and
acquiring, according to the interactive information, user associated information as at least a part of the auxiliary preference information;
generating, according to the recipe preference characteristic and the auxiliary preference information, a recommended recipe matching the cooking device product information; and
transmitting the recommended recipe to the cooking service application.

2. The recipe pushing method according to claim 1, wherein receiving the cooking device product information includes:
receiving the cooking device product information obtained by the terminal device scanning a two-dimensional code of the cooking device.

3. The recipe pushing method according to claim 1, wherein extracting the recipe preference characteristic includes:
detecting whether a browsing duration of the user on a target recipe in the cooking service application is greater than or equal to a preset threshold value; and
in response to the browsing duration being greater than or equal to the preset threshold value, extracting the recipe preference characteristic according to information of the target recipe.

4. The recipe pushing method according to claim 1, wherein extracting the recipe preference characteristic includes:
detecting whether a browsing frequency of a user on a target recipe in the cooking service application is greater than or equal to a preset threshold value; and
in response to the browsing frequency being greater than or equal to the preset threshold value, extracting the recipe preference characteristic according to information of the target recipe.

5. The recipe pushing method according to claim 1, wherein extracting the recipe preference characteristic includes:
detecting whether a browsing duration of the user on a target recipe in the cooking service application is greater than or equal to a preset first threshold value and whether a browsing frequency of the user on the target recipe is greater than or equal to a preset second threshold value; and
in response to the browsing duration being greater than or equal to the preset first threshold value and the browsing frequency is greater than or equal to the preset second threshold value, extracting the recipe preference characteristic according to information of the target recipe.

6. The recipe pushing method according to claim 1, wherein acquiring the auxiliary preference information further includes:
receiving an application login request including user information transmitted by the terminal device;
permitting a user account corresponding to the user information to log in the cooking service application in response to the user information being verified to be legal according to pre-stored registration information; and
acquiring user attribute information according to the registration information.

7. The recipe pushing method according to claim 1, wherein acquiring the auxiliary preference information further includes:
acquiring location information of the user.

8. The recipe pushing method according to claim 1, further comprising, after transmitting the recommended recipe to the cooking service application:

receiving evaluation information transmitted by the terminal device via the cooking service application; and
optimizing the recommended recipe according to the evaluation information.

9. The recipe pushing method according to claim 1, wherein extracting the recipe preference characteristic of a user according to the history of the user browsing recipes in the cooking service application and the preset filtering condition includes:
   determining the recipe preference characteristic of the user according to at least a common feature of a plurality of target recipes in the cooking service application that have been browsed by the user and satisfy the preset filtering condition.

10. A non-transitory machine readable storage medium storing instructions that, when executed, cause a cooking device to:
   receive cooking device product information of a cooking device transmitted by a terminal device via a cooking service application;
   extract a recipe preference characteristic of a user according to a history of the user browsing recipes in the cooking service application and a preset filtering condition;
   acquire auxiliary preference information of the user by:
      acquiring interactive information related to an interaction between the user and another application via the cooking service application; and
      acquiring, according to the interactive information, user associated information as at least a part of the auxiliary preference information;
   generate, according to the recipe preference characteristic and the auxiliary preference information, a recommended recipe matching the cooking device product information; and
   transmit the recommended recipe to the cooking service application.

11. A recipe pushing apparatus comprising:
   a processor; and
   a storage medium storing a program that, when executed, causes the processor to:
      receive cooking device product information of cooking device transmitted by a terminal device via a cooking service application;
      extract a recipe preference characteristic of a user according to a history of the user browsing recipes in the cooking service application and a preset filtering condition;
      acquire auxiliary preference information of the user by:
         acquiring interactive information related to an interaction between the user and another application via the cooking service application; and
         acquiring, according to the interactive information, user associated information as at least a part of the auxiliary preference information;
      generate, according to the recipe preference characteristic and the auxiliary preference information, a recommended recipe matching the cooking device product information; and
      transmit the recommended recipe to the cooking service application.

12. The recipe pushing apparatus according to claim 11, wherein the cooking device product information is obtained by the terminal device scanning a two-dimensional code of the cooking device.

13. The recipe pushing apparatus according to claim 11, wherein the program causes the processor to extract the recipe preference characteristic by:
   detecting whether a browsing duration of the user on a target recipe in the cooking service application is greater than or equal to a preset threshold value; and
   in response to the browsing duration being greater than or equal to the preset threshold value, extracting the recipe preference characteristic according to information of the target recipe.

14. The recipe pushing apparatus according to claim 11, wherein the program causes the processor to extract the recipe preference characteristic by:
   detecting whether a browsing frequency of the user on a target recipe in the cooking service application is greater than or equal to a preset threshold value; and
   in response to the browsing frequency being greater than or equal to the preset threshold value, extracting the recipe preference characteristic according to information of the target recipe.

15. The recipe pushing apparatus according to claim 11, wherein the program causes the processor to acquire the auxiliary preference information further by:
   receiving an application login request including user information transmitted by the terminal device;
   permitting a user account corresponding to the user information to log in the cooking service application in response to the user information being verified to be legal according to pre-stored registration information; and
   acquiring user attribute information according to the registration information.

16. The recipe pushing apparatus according to claim 11, wherein the program causes the processor to acquire the auxiliary preference information further by:
   acquiring location information of the user.

17. The recipe pushing apparatus according to claim 11, wherein the program further causes the processor to:
   receive evaluation information transmitted by the terminal device via the cooking service application; and
   optimize the recommended recipe according to the evaluation information.

* * * * *